US010213622B2

(12) United States Patent
Bharat et al.

(10) Patent No.: US 10,213,622 B2
(45) Date of Patent: Feb. 26, 2019

(54) REAL-TIME QUANTIFICATION OF SKIN BURNS IN EXTERNAL BEAM RADIATION THERAPY

(71) Applicant: KONINKLIJKE PHILIPS N.V., Eindhoven (NL)

(72) Inventors: Shyam Bharat, Arlington, MA (US); Christopher Stephen Hall, Kirkland, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 445 days.

(21) Appl. No.: 14/893,536

(22) PCT Filed: Jun. 25, 2014

(86) PCT No.: PCT/IB2014/062574
§ 371 (c)(1),
(2) Date: Nov. 24, 2015

(87) PCT Pub. No.: WO2014/207663
PCT Pub. Date: Dec. 31, 2014

(65) Prior Publication Data
US 2016/0136455 A1    May 19, 2016

Related U.S. Application Data

(60) Provisional application No. 61/839,911, filed on Jun. 27, 2013.

(51) Int. Cl.
*A61N 5/10*    (2006.01)

(52) U.S. Cl.
CPC ......... *A61N 5/1039* (2013.01); *A61N 5/1038* (2013.01); *A61N 5/1067* (2013.01); *A61N 2005/1054* (2013.01); *A61N 2005/1058* (2013.01); *A61N 2005/1059* (2013.01)

(58) Field of Classification Search
CPC .. A61N 5/1038; A61N 5/1039; A61N 5/1067; A61N 2005/1054; A61N 2005/1058; A61N 2005/1059
USPC .................... 600/1, 476–478; 378/65
See application file for complete search history.

(56) References Cited

U.S. PATENT DOCUMENTS

| | | | |
|---|---|---|---|
| 6,411,907 B1 | 6/2002 | Lu et al. | |
| 7,855,656 B2 * | 12/2010 | Maschke | A61B 6/102 340/573.1 |
| 8,160,205 B2 | 4/2012 | Saracen et al. | |
| 8,641,592 B2 * | 2/2014 | Yu | A61N 5/1049 250/492.1 |
| 9,486,647 B2 * | 11/2016 | Bergfjord | A61N 5/1048 |
| 2014/0114150 A1 | 4/2014 | Pogne et al. | |
| 2014/0321728 A1 | 10/2014 | Chin | |

FOREIGN PATENT DOCUMENTS

JP        2004337217 A    12/2004

* cited by examiner

*Primary Examiner* — Samuel Gilbert

(57) ABSTRACT

A system for radiation therapy include an imaging device (108) configured to scan an area of interest for tissue undergoing radiation therapy to collect one or more images of the tissue. An interpretation module (110) is configured to receive the one or more images of the tissue to determine a burn status of the tissue and provide adjustments for a radiation treatment plan in accordance with the burn status.

14 Claims, 4 Drawing Sheets

REAL-TIME QUANTIFICATION OF SKIN BURNS IN EXTERNAL BEAM RADIATION THERAPY

CROSS-REFERENCE TO PRIOR APPLICATIONS

This application is the U.S. National Phase application under 35 U.S.C. § 371 of International Application Serial No. PCT/IB2014/062574, filed on Jun. 25, 2014, which claims the benefit of U.S. Application Ser. No. 61/839,911, filed on Jun. 27, 2013. These applications are hereby incorporated by reference herein.

BACKGROUND

Technical Field

This disclosure relates to medical instruments and more particularly to systems and methods for measuring changes in skin during operative procedures.

Description of the Related Art

External Beam Radiation Therapy (EBRT) is an important and commonly used treatment modality for cancer; however, it has many deleterious side-effects. In EBRT for breast cancer, skin burn is a serious side-effect of the treatment. Some EBRT-induced skin reactions are immediate, while others may take days or weeks to occur. The skin reactions can occur on any part of the skin that is in the path of the radiation beam. Since EBRT treatments involve the use of radiation beams from multiple directions around the patient, skin burns in the case of breast EBRT can occur in the shoulder, back, neck and contra-lateral breast. Skin reactions such as these cause a great deal of pain and discomfort to the patient, in addition to other side-effects. In some cases, extreme skin reactions may lead to the generation of new cancerous cells. Currently, there is no technology available to quantify and/or avoid skin burns resulting from EBRT treatments.

SUMMARY

In accordance with the present principles, a system for radiation therapy includes an imaging device configured to scan an area of interest for tissue undergoing radiation therapy to collect one or more images of the tissue. An interpretation module is configured to receive the one or more images of the tissue to determine a burn status of the tissue and provide adjustments for a radiation treatment plan in accordance with the burn status.

Another system for radiation therapy includes a portable imaging device configured to scan an area of interest for tissue undergoing radiation therapy. A robotically controlled arm, on which the portable imaging device is mounted, is controlled to avoid interference with radiation beams for the radiation therapy. An interpretation module is configured to receive images of the tissue collected by the imaging device to determine a burn status of the tissue and provide adjustments for a radiation treatment plan in accordance with the burn status.

A method for radiation therapy includes controlling a position of an imaging device to avoid interference with radiation beams for the radiation therapy; imaging an area of interest for tissue undergoing radiation therapy using the imaging device; interpreting images of the tissue collected by the imaging device to determine a burn status of the tissue; and adjusting further treatment in accordance with the burn status.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
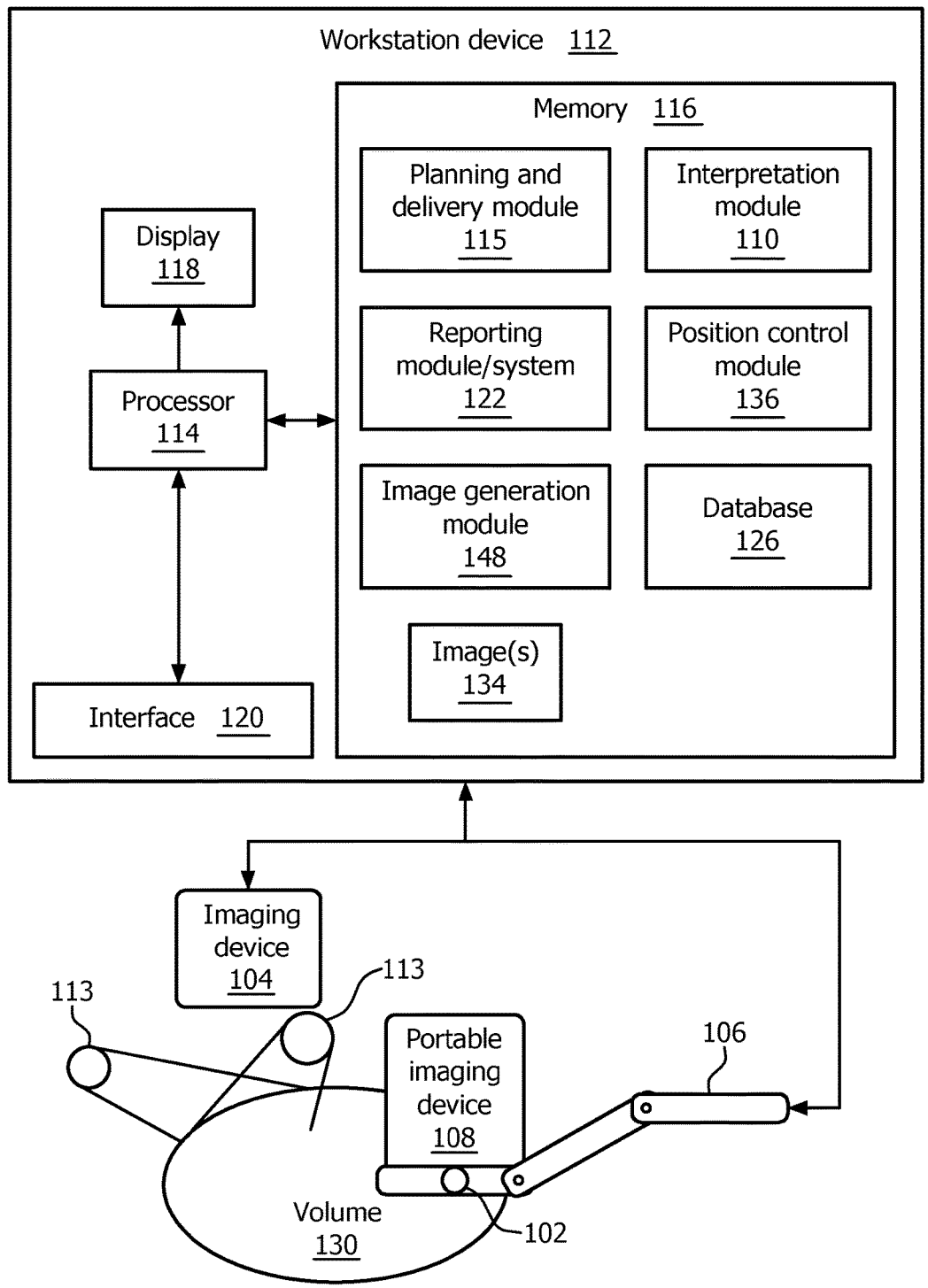
FIG. 1 is a block/flow diagram showing a radiation therapy system which employs skin burn information in accordance with one embodiment.

In accordance with the present principles, systems and methods are provided for preventing and/or mitigating skin burns in patients as a result of external bean radiation therapy (EBRT). The present principles may be employed with adaptive radiation therapy (RT) planning and delivery schemes that may use the minimization of skin reactions as an additional optimization parameter in the design of adaptive treatment plans. In some embodiments, optical or photoacoustic imaging technology is employed to quantitatively image the progression of radiation-induced skin burns, in real-time during EBRT delivery and at various intervals after EBRT delivery.

Skin burns are known to change the levels of hemoglobin and water content in the affected regions in addition to changing local perfusion patterns with increased vasodilation. Diffuse optical tomography (DOT) imaging techniques measure the tissue concentrations of hemoglobin, water and oxygen saturation. Suitable imaging protocols are described in conjunction with existing RT workflows, to obtain real-time updates of skin burn progression during EBRT delivery. Based on the imaging data, corrective action can be proposed to the patient to pre-empt the subsequent occurrence of burn-related symptoms in the days and weeks following treatment (e.g., icing, creams, gels etc.).

Intermittent imaging after EBRT delivery can further monitor late skin reactions and may also help ascertain the efficacy of any corrective treatments being used to alleviate the burns. In addition, population-based statistics on skin burn patterns may be developed and related to RT plan characteristics, to permit the creation of intensity-modulated RT (IMRT) plans with "skin burn reduction" as an additional dose optimization parameter.

With a minimal workflow overload, the present methods monitor and reduce skin burn during EBRT delivery. A new parameter for adaptive treatment planning in EBRT is also introduced. Reduction in RT side-effects such as skin burns leads to improved quality of life for patients, post-RT.

It should be understood that the present invention will be described in terms of medical instruments and procedures; however, the teachings of the present invention are much broader and should not be limited by the described examples. In some embodiments, the present principles are employed in tracking or analyzing complex biological or mechanical systems. In particular, the present principles are applicable to tracking procedures of biological systems, procedures in all areas of the body such as, the skin, but may be useful for internal organs, such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk read only memory (CD-ROM), compact disk read/write (CD-R/W), Blu-Ray™ and DVD.

Referring now to the drawings in which like numerals represent the same or similar elements and initially to FIG. 1, a system 100 for evaluating skin burns or skin burn potential is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store a planning and delivery module 115 configured to plan and control a radiation therapy session or sessions by controlling radiation sources, imaging devices, etc. An interpretation module 110 is configured to receive one or more images of tissue in an area of interest to determine a burn status of the tissue. The interpretation module 110 can provide suggestions for adjustments for a radiation treatment plan in accordance with the burn status. The treatment plan may be a treatment plan stored and executed by the planning and delivery module 115. The interpretation module 110 employs feedback, e.g., from images, for image maps, or from measurements (optical or acoustical) collected from the tissue of interest. The feedback is employed to interpret the images or data and record changes over time. Module 110 is configured to use the optical, acoustical or image feedback to evaluate skin of a patient in real-time to determine burns or potential burns.

The system 100 includes one or more imaging devices 104, which are to be employed in conjunction with RT delivery. The imaging devices 104 are sensitive to changes in local perfusion patterns on skin of a patient. The imaging devices 104 may include a device or devices to perform one or more of diffuse optical spectroscopy (DOS), diffuse optical imaging (DOI), photoacoustic computed tomography (PAT), photoacoustic microscopy (PAM), laser Doppler perfusion imaging (LDPI), polarization sensitive optical coherence tomography (PSOCT), high frequency ultrasound, etc. The imaging modality needs to be capable of differentiating change in the skin during a procedure. In one embodiment, diffuse optical spectroscopy (DOS) is an optical technique that quantitatively measures near-infrared (NIR, 650 to 1000 nm) absorption and reduced scattering spectra. Absorption spectra are employed to calculate the tissue concentrations of oxygenated and deoxygenated hemoglobin, water and bulk lipid, which are the dominant NIR molecular absorbers in breast tissues. DOS does not need exogenous contrast and provides rapid quantitative and functional information of the above quantities (imaging updates every 10 seconds).

DOS employs a large spectral bandwidth, but has a low spatial sampling rate. Diffuse optical imaging (DOI) is a complementary tool that provides a good sampling distribution, but with a low spectral bandwidth. Thus, DOI can be tuned to provide absorption characteristics of specific chromophores, e.g., hemoglobin, water etc. Chromophore concentrations can be estimated directly from the absorption spectra measurements. Some of the physiological changes observed in burned skin are the markedly different levels of hemoglobin and water. Periods of respiratory insufficiency have been known to occur in severe skin burns. The oxygen supply to tissues during these periods is regulated by changes in blood flow, hemoglobin mass and variations in the oxygen-releasing capacity of hemoglobin. Hence, a quantifiable measurement of the mass of hemoglobin/amount of water in a given spatial region at any instant is representative of the physiological changes occurring that can result in (radiation-induced) skin burns.

In particularly useful embodiments, two or more imaging modalities may be employed concurrently to ensure a more accurate result when evaluating skin burns. The imaging devices 104 may include portable capabilities and may include imaging equipment or a portable imaging device 108 on a robotically controlled arm 106. The robotically controlled arm 106, if employed, may include multiple degrees of freedom to position the portable imaging device 108 appropriately so as to not interfere with a currently active radiation beam.

The system 100 includes one or more radiation sources 113 for radiation therapy (RT) delivery during a procedure. The sources 113 may be orchestrated using the planning module 115 to deliver predetermined amounts of radiation at predetermined locations for predetermined amounts of time in accordance with a plan. It should be understood that the robotic arm 106 with the imaging device 108 mounted thereon may be programmed along with the plan to prevent interference with the radiation beams from the sources 113.

During a procedure, at least intermittent measurements of "skin burn" after RT delivery are provided. This may include imaging one or more areas known to experience skin burn or potentially experience skin burn as a result of the radiation exposure. The images of the skin areas may be compared to previous images to identify changes to the tissue, or the images or image maps may be employed with the one or more imaging devices 104, which are sensitive to changes in local perfusion patterns on the skin of the patient. The checks on the skin may be performed during the procedure in between radiation periods, during radiation periods and/or continuously during the procedure. A display 118 may be provided to view two or three dimensional (2D or 3D) images of spatial patterns in tissue indicating a magnitude of skin burn. Real-time measurements of skin burn during radiation therapy delivery may be provided.

The skin burn status may be employed during the procedure as real-time feedback to adjust the parameters of the radiation therapy. In one embodiment, adaptive radiation therapy in the planning and delivery module 115 may incorporate "skin burn" as a parameter to be minimized in the dose optimization procedure. For example, doses associated with skin burn degrees may be monitored when generating a plan or during a procedure to determine whether a different approach or different parameters should be employed to minimize skin burns.

The workstation 112 may include or work with a position control module 136 configured to control the motion of the robotic arm 106. The motion of the robotic arm 106 may be scripted along with the radiation plan stored in the planning and delivery module 115. Alternately, the robotic arm 106 may include a tracking device 102 to provide feedback on its position so that positional interference does not occur between the radiation beams and the robotic arm 106 (and its accessories) during a procedure.

The memory 116 may include a reporting module 122 to suggest a course of therapy to treat burn injuries (e.g., location of predicted burn symptoms). For example, in one embodiment, radiation exposure areas may have a cumulative radiation dose recorded for each area to predict areas of burns or potential burns. Based upon the location of burn areas and potential burn areas and the severity of the dose, treatment options may be output by the reporting module 122. The treatment options may include applying ice, creams, gels, etc. to defined areas in a report. The report is customized to the individual based upon the procedure and the events during the procedure.

The collected 'skin burn' data maps can be input to the reporting module 122, which considers the severity and locations of the any skin burns for predicting present and/or future effects. The reporting module 122 can suggest medication(s) (e.g., lotions, ointments, creams, etc.) to pre-empt the occurrence of burn symptoms in the days and weeks following treatment, based on the recorded 'skin burn' data during or after RT delivery. For example, certain anatomical locations may be more prone to development of soreness, redness, rash, etc.

The planning and delivery module 115 may include or may access a database 126 of skin burn patterns from previous procedures. The database 126 derives and stores correlations with treatment plan characteristics, patient geometry, etc., to generate future treatment plans with 'skin burn' (reduction) as a dose optimization parameter. The adaptive planning and delivery module 115 may employ the stored data and adapt a treatment plan or adjust a remaining treatment plan based on the data in the database 126. In addition or in the alternative, the current skin burn data and/or the data in the database 126 may be employed as feedback for adjusting the treatment plan, e.g., as changes occur. Minimization of skin burn during RT delivery may be employed as an additional optimization parameter for creating optimized RT plans at the planning stage or to update a plan.

In one embodiment, workstation 112 includes an image generation module 148 configured to receive feedback from the imaging devices 104 and record accumulated image data to determine potential locations for skin burns. An image 134 can be displayed on the display device 118 for comparison with previous images and/or measurements. The previous measurements may include the status of water, hemoglobin, etc., which can be measured using the imaging devices 104. Workstation 112 includes the display 118 for viewing images (134) of a subject (patient) or volume 130. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

By imaging, in real-time, the physiological changes occurring in tissue during EBRT delivery, it is possible to predict location and intensity of burn-related symptoms that may eventually manifest in the days and weeks following RT. This information may be utilized to determine appropriate corrective schemes to reduce discomfort to the patient. A simple example includes determining an optimum location for the application of external ointments, creams, etc. to pre-empt the appearance of burn symptoms. Subsequent to RT delivery, intermittent imaging may further allow the monitoring of late-effect skin burns and/or the reduction of burn symptoms as a result of corrective treatment. Another advantage may be realized if population-based statistics (e.g., stored in the database 126) of skin burns are utilized to develop adaptive planning strategies that include "skin burn" as a parameter to be minimized in the dose optimization paradigm.

Figure 2:
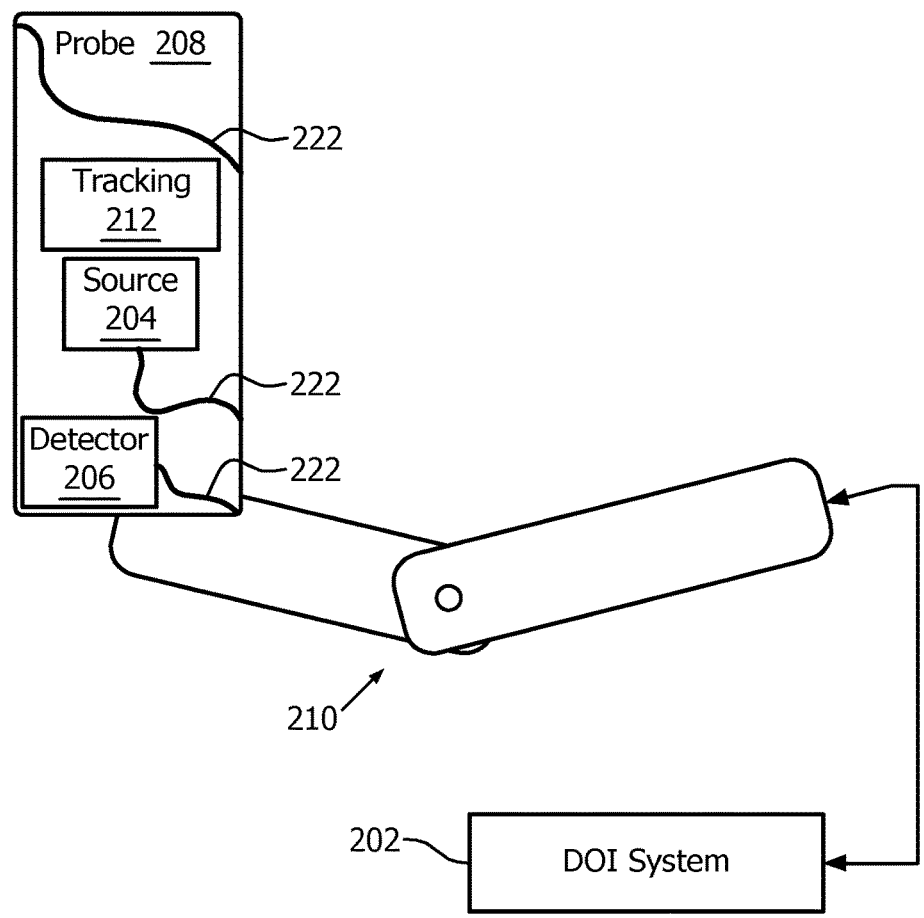
FIG. 2 is a block/flow diagram showing a portable imager mounted on a controlled arm for avoiding interference with radiation beams in accordance with one embodiment.

Referring to FIG. 2, in one embodiment, the one or more imaging devices 104 may include a DOI system 202 having a portable robotically-held probe 208. A robotic arm 210, preferably free to move with multiple degrees of freedom, is utilized to position the probe 208, which includes a portable imaging device or scanner. In one embodiment, the robotic arm 210 is tracked using a tracking mechanism 212. The tracking mechanism 212 may include an electromagnetic tracking device, a fiber optic shape sensing system, kinematic equations which rely on the robotic linkages and known movements to define its motion, etc. The tracking mechanism 212 provides feedback on the position of the robotic arm 210 and its resident devices to ensure that it does not interfere with radiation beams during a procedure. Since the positions of the radiation beams will be identified and known in space, the tracking device 212 will identify the location of the robotic arm 210 for comparison to ensure that no interference occurs.

The probe 208 may include optical fibers 222 for illumination (e.g., 5-10 fibers, although other numbers of fibers are contemplated) and detection (e.g., 50-200 fibers, although other numbers of fibers are contemplated). A laser diode source 204 is connected to the optical fibers for illumination, and an intensified charge-coupled device (CCD) camera detector 206 is connected to the optical fibers for detection. Simultaneous illumination and detection can be carried out using different optical fibers, for real-time 2D imaging, e.g., continuous wave (CW) optical measurements may be made. Frequency domain (FD) or other measurements are also contemplated.

The DOI system 202 includes a tuning capability to image a range of variable depths in the tissue, since skin burns can range from superficial (0.07-0.12 mm) to deep (>2 mm). Other technologies, such as, photoacoustic microscopy (PAM), laser Doppler perfusion imaging (LDPI), polarization sensitive optical coherence tomography (PSOCT) etc. can also be incorporated in such a portable scanner/probe 208.

Figure 3:
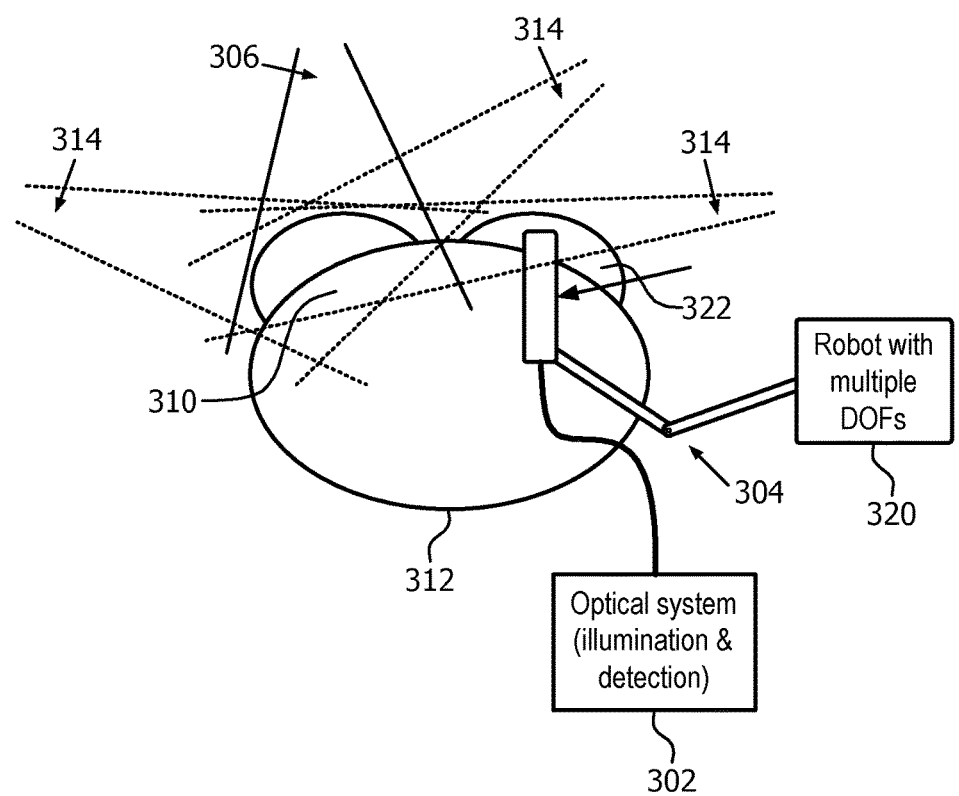
FIG. 3 is a diagram showing multiple beam directions to further demonstrate avoiding interference with radiation beams by a portable imager mounted on a controlled arm in accordance with one embodiment.

Referring to FIG. 3, a schematic diagram shows optical and/or photoacoustic imaging implemented in a portable scanner or imager 302 that is integrated with the EBRT delivery protocol (e.g., stored in memory 116 of workstation 112, FIG. 1) and controlled by a robot or other fixture 320. One constraint on a robotic arm 304 is that the portable imager 302 should not interfere with a path of an active beam 306. To achieve this, a position control algorithm (e.g., stored as position control module 136, FIG. 1), controls the position of the portable imager 302 based on the currently active RT beam 306 and the known temporal pattern of line positions obtained from the RT planning system 115 (FIG. 1) and/or a record and verify (R&V) system, which may be implemented by the workstation 112. Depending on skin regions 310 that will be irradiated on a patient 312, the portable imager 302 can be sequentially moved to all needed positions, subject to the constraint that it does not interfere with the path of the currently active beam 306. The currently active beam 306 may be switched to other beam directions (inactive beams 314) using other sources or the same repositioned source. The positions of the beams are known as well as the position of the portable imager 302. The algorithm employs these positions and other constraints, e.g., the sizes of the beams or scanner equipment, accessories or other devices employed during therapy, etc., to avoid any overlap between the positions of the portable imager 302 and the active beam 306.

In one embodiment, a real-time readout of chromophore concentrations can be displayed as a measure of "skin burn" on a console/display 118 (FIG. 1). Multiple displays or display panels may be provided. For example, one display may show the values of 'skin burn' updated on a real-time image. Another display may show the cumulative burn effects of the RT delivery, etc. An alternative method to robotically moving the sensing system may include using the RT planning system 115 to suggest an optimal static location for monitoring the largest field of view during the procedure. Other configurations and displays are also contemplated.

As can illustratively be seen in FIG. 3, skin burns may occur by exposure to multiple beams. For example, in breast EBRT, at least one of the beams 306, 314 almost always intersects a contra-lateral breast 322 and possibly other normal structures like the shoulder, neck, etc. Therefore, vigilance in these areas using the portable imager 302 can assist in planning to avoid the occurrence of skin burns where possible.

Figure 4:
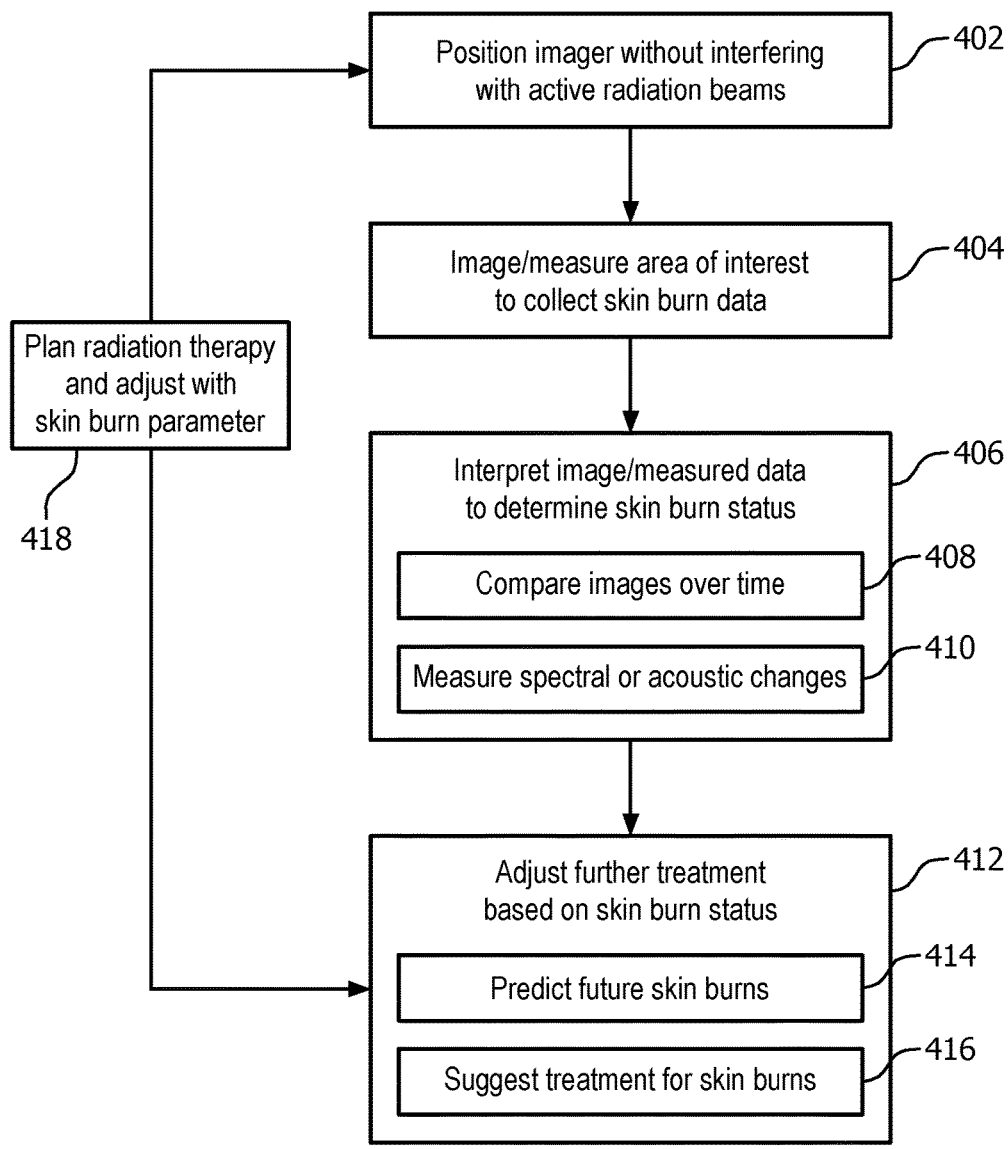
FIG. 4 is a flow diagram showing a method for radiation therapy using skin burn status in accordance with an illustrative embodiment.

Referring to FIG. 4, a method for radiation therapy, which employs skin burn status, is shown in accordance with illustrative embodiments. In block 402, a position of an imaging device is controlled to avoid interference with radiation beams for the radiation therapy. The position of the imaging device may be controlled in accordance with a script or plan, which involves knowing positions of all active the radiation beams and avoiding interference by the imaging device or devices. The imaging device may be mounted on a robotically controlled arm or other fixture.

In block 404, an area of interest for tissue undergoing radiation therapy is imaged or measured (e.g., optically/spectrally or acoustically) using the imaging device. Imaging an area of interest includes employing one or more of: diffuse optical spectroscopy (DOS), diffuse optical imaging (DOI), photoacoustic computed tomography (PAT), photoacoustic microscopy (PAM), laser Doppler perfusion imaging (LDPI), polarization sensitive optical coherence tomography (PSOCT), high frequency ultrasound, etc. Other technologies may also be employed. In addition or instead, comparisons between photographic images may be compared over time to determine a burn status.

In block 406, collected images (and/or measurements derived therefrom) are interpreted for the tissue to determine a burn status of the tissue. The magnitude of the burn may be determined based upon color changes/absorption spectra although density (acoustic changes) and other properties may be employed. Interpreting the images may include comparing images over time in block 408, and/or measuring absorption spectra of one or more of hemoglobin, water and lipids in block 410. Other methods may be employed for interpreting burns as well.

In block 412, further treatment is adjusted in accordance with the burn status. This may include real-time changes to a plan or include post radiation treatment for the burns incurred. In block 414, further treatment adjustments may include predicting future skin burns based upon images of the tissue collected by the imaging device and the radiation therapy underwent by a patient. This may include using probabilistic and/or historic data to determine potential burn areas and severity. In block 416, skin burn treatment may be suggested by a reporting system or module and is preferably customized to the radiation therapy received and/or the patient receiving it. Burn effects may also be measured post-procedure and employed to determine the skin burn treatment plan or to update the skin burn treatment plan.

In block 418, radiation therapy may be planned based at least in part upon a skin burn parameter employed to minimize skin burns in a plan. This may include an initial plan or an updated plan based upon real-time burn data collected during a procedure.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and e) no specific sequence of acts is intended to be required unless specifically indicated.

Having described preferred embodiments for real-time quantification of skin burns in external beam radiation therapy (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

Then invention claimed is:

1. A system for monitoring radiation therapy, comprising:
an imaging device configured to scan an area of interest for tissue undergoing radiation therapy to collect one or more images of the tissue; and
an interpretation module configured to receive the one or more images of the tissue to determine a burn status, including a measurement of a burn of the tissue, and provide adjustments for a radiation treatment plan in accordance with the burn status.

2. The system as recited in claim 1, wherein the imaging device includes a portable imager configured to move to avoid interference with radiation beams.

3. The system as recited in claim 2, wherein the portable imager is mounted on a robot and the robot is controlled to avoid interference with the radiation beams.

4. The system as recited in claim 1, wherein the imaging device includes one or more of: diffuse optical spectroscopy (DOS), diffuse optical imaging (DOI), photoacoustic computed tomography (PAT), photoacoustic microscopy (PAM), laser Doppler perfusion imaging (LDPI), polarization sensitive optical coherence tomography (PSOCT), and high frequency ultrasound.

5. The system as recited in claim 1, wherein the burn status is determined based upon absorption spectra of one or more of hemoglobin, water and lipids.

6. The system as recited in claim 1, further comprising a planning and delivery module configured to plan radiation therapy and include a skin burn parameter employed to minimize skin burns in the plan.

7. The system as recited in claim 6, wherein the planning and delivery module adjusts the plan in accordance with the burn status.

8. The system as recited in claim 1, further comprising a reporting system configured to report skin burn treatment customized to the radiation therapy received.

9. The system as recited in claim 1 wherein:
the imagining device is a portable imaging device;
the system further comprising a robotically controlled arm, on which the portable imaging device is mounted, the arm being controlled to avoid interference with radiation beams for the radiation therapy.

10. The system as recited in claim 9, wherein the imaging device includes one or more of: diffuse optical spectroscopy (DOS), diffuse optical imaging (DOI), photoacoustic computed tomography (PAT), photoacoustic microscopy (PAM), laser Doppler perfusion imaging (LDPI), polarization sensitive optical coherence tomography (PSOCT), and high frequency ultrasound.

11. The system as recited in claim 9, wherein the burn status is determined based upon absorption spectra of one or more of hemoglobin, water and lipids.

12. The system as recited in claim 9, further comprising a planning and delivery module configured to plan radiation therapy and include a skin burn parameter employed to minimize skin burns in the plan.

13. The system as recited in claim 12, wherein the planning and delivery module adjusts the plan in accordance with the burn status.

14. The system as recited in claim 9, further comprising a reporting system configured to report skin burn treatment customized to the radiation therapy received.

* * * * *